United States Patent [19]

Dobkin

[11] Patent Number: 4,659,563

[45] Date of Patent: Apr. 21, 1987

[54] HIGH TITER ANTI-RESPIRATORY SYNCYTIAL VIRUS INTRAVENOUS IMMUNE GLOBULIN

[75] Inventor: Milton B. Dobkin, Lafayette, Calif.

[73] Assignee: Miles Laboratories, Inc., Elkhart, Ind.

[21] Appl. No.: 822,560

[22] Filed: Jan. 27, 1986

[51] Int. Cl.[4] .............................................. A61K 39/42
[52] U.S. Cl. ........................................ 424/86; 424/85; 530/387
[58] Field of Search ...................... 424/85, 86; 530/387

[56] References Cited

U.S. PATENT DOCUMENTS

| | | | |
|---|---|---|---|
| 3,903,262 | 9/1975 | Pappenhagen et al. | 424/85 |
| 4,174,388 | 11/1979 | McAleer et al. | 424/86 |
| 4,186,192 | 1/1980 | Lundblad et al. | 424/85 |
| 4,396,608 | 8/1983 | Tenold | 424/85 |
| 4,499,073 | 2/1985 | Tenold | 424/85 |

OTHER PUBLICATIONS

Richardson et al., C.A. 89 #74058j (1978) of Infect. Immun. 1978 20(3): 660-4, "Enzyme-Linked Immunosorbent Assay for Measurement of Serological Response to Respiratory Syncytial Virus Infection".

*Primary Examiner*—Shep K. Rose
*Attorney, Agent, or Firm*—James A. Giblin; Pamela A. Simonton

[57] ABSTRACT

Normal plasma from donors who have not necessarily been vaccinated with a respiratory syncytial virus vaccine can be screened for higher than normal titers of naturally occurring antibody to respiratory syncytial virus (e.g. minimum ELISA titer of at least 1:110,000). Those plasmas with high titers of such antibody can be pooled and fractionated to give hyperimmune globulin. The product may be treated to render it suitable for intravenous injection. Patients with respiratory syncytial virus infection or at risk of such infection, may receive the present product to raise serum antibody titers to respiratory syncytial virus. Resultant product has an ELISA anti-RSV titer of at least about 1:250,000.

8 Claims, No Drawings

HIGH TITER ANTI-RESPIRATORY SYNCYTIAL VIRUS INTRAVENOUS IMMUNE GLOBULIN

BACKGROUND OF THE INVENTION

1. Field of the Invention

This invention relates to and has among its objects a novel immune globulin and novel methods for its production. Particularly, the invention is concerned with an intravenously injectable immune globulin having a high titer of naturally occurring antibody to respiratory syncytial virus (RSV). Further objects of the invention will be evident from the following description wherein parts and percentages are by weight unless otherwise specified.

2. Description of the Prior Art

Respiratory syncytial virus is considered the most important cause of severe respiratory disease in infants and young children. It can also be an important cause of lower respiratory tract disease in the elderly. In the United States alone it has been reported that this virus causes pneumonia, bronchitis and croup in approximately 4 million children each year, resulting in about 4500 deaths. In the western world it is the major cause for hospitalization of children [*National Research Council News Report*, 35, 9 (1985), Stott, E. J. et al, *Archives of Virology*, 84:1–52 (1985), and W. H. O. Scientific Group, *World Health Organization Technical Report Series* 642 (1980)].

In industrial areas of Great Britain the annual rate of hospital admissions of children between 1 and 3 months of age, as a result of RSV infection, has been reported to be 24.5 per 1000 children [Stott, E. J. et al, *Archives of Virology*, 84:1–52 (1985)].

At the present time there is no vaccine available to prevent this disease. An inactivated vaccine developed nearly 25 years ago not only was ineffective, but appeared to potentiate more severe disease in vaccinated children as compared with placebo controls [Kapikian, A. Z. et al, *American Journal of Epidemiology*, 89:405–21 (1969) and Kim, H. W. et al, *American Journal of Epidemiology*, 89:422–34 (1969)].

Although the disease is most severe during the first few months of life, at a time when moderate levels of maternal antibody are present, recent studies in an animal model indicate that maternal antibody is ineffective below a critical level [Prince, G. A., et al, *Journal of Virology*, 55:517–20 (1985)].

Hemming et al, [*J. Infectious Diseases*, 152, 1033 (1985)], disclose the results of a study of passive immunotherapy for respiratory syncytial virus infections in the respiratory tract of a primate model, which showed that the infusion of human intravenous immune globulin (prepared from plasma having an antibody titer to the virus in the normal range) significantly reduced the amounts of virus shed from the noses and airways of RSV-infected owl monkeys.

Hyperimmune globulins, i.e., immune globulins having higher than normal titers of a particular antibody, are therapeutically useful in treating patients deficient or in need of that particular antibody. For example, tetanus hyperimmune globulin is useful in treating tetanus, and rabies hyperimmune globulin, rabies. It is well known that hyperimmune globulins can be produced from plasma or serum obtained from selected donors who have significantly higher titers for a specific antibody than is normally found in the average population. These donors have either been recently immunized with a particular vaccine (U.S. Pat. No. 4,174,388) or else they have recently recovered from an infection or disease [Stiehm, *Pediatrics*, Vol. 63, No. 1, 301–319 (1979)].

Accordingly, there is a need for an RSV immune globulin product having a higher than normal titer of antibody to RSV, especially one that may be administered intravenously.

SUMMARY OF THE INVENTION

I have found that normal fresh plasma from normal donors who have not necessarily been vaccinated with an RSV vaccine can be usefully screened for higher than normal titers of antibody to RSV. Those plasmas with antibody titers greater than about 1:110,000, determined by means of an enzyme-linked immunosorbent assay (ELISA), can be pooled and then fractionated to give a hyperimmune globulin or, more specifically, a high titer anti-respiratory syncytial immune globulin, that, by further processing, may be administered intravenously. This result is surprising because it is unexpected that plasma from normal, unvaccinated donors would have a titer of antibody to RSV high enough to yield an RSV hyperimmune globulin which would be effective in treating RSV infections by intravenous administration.

One obvious advantage of the invention is that normal donors need not be given an RSV vaccine. Consequently, the risks inherent in such a practice are avoided. Another advantage of the invention is that the hyperimmune globulin, when given intravenously, makes antibodies to RSV immediately available. Another advantage resides in avoiding patient discomfort associated with intramuscular administration. Other advantages are elimination of a delay of several days for RSV antibodies to reach a peak in the circulation, and elimination of local degradation. Furthermore, less product needs to be administered intravenously in order to achieve the same level of antibody obtained with an intramuscularly administered product or higher doses can be administered intravenously to provide higher titers which would otherwise be difficult to obtain by intramuscular administration.

DESCRIPTION OF THE PREFERRED EMBODIMENTS

These and other advantages of the present invention may be obtained in the following manner.

Normal plasma from a donor is tested for naturally occurring antibody to RSV employing an ELISA or other equally sensitive screening method (e.g., RIA) at an equivalent titer. To be effective in the method and product according to this invention, the "selected" plasma from donors should have a titer of antibody to RSV about 5 times the titer of antibody to RSV found in "normal" donors [*Clin. Exp. Immunol.*, 52, 412–422 (1983)].

The expression "about 5 times the titer of antibody to RSV" is meant to include levels which may be slightly below 5 times or slightly greater than 5 times but which result in an average of about 5 times the titer of antibody to RSV found in normal donors. I have found that the geometric mean titer of antibody to RSV, in most donors, is about 1:25,000 (hereafter referred to as "normal" titer) and that about 2–4% of plasma donors have a titer of antibody to RSV about 5 times the normal titer ("selected" titer). More specifically, I have found that a geometric mean titer in 39 "selected" plasma samples is about 1:110,000. Accordingly, to be effective in the method and product of this invention, the "selected" plasma from donors should have a titer of antibody to RSV equal to or greater than about 1:110,000.

Generally, as a result of the manufacturing process, the immune globulin produced from plasma has been found to have a titer of antibody about 5 times the titer of antibody found in the starting plasma. Thus, it is expected that the titer of antibody to RSV in the immune globulin produced from normal plasma, hereafter referred to as normal immune globulin, will be about 1:125,000. However, I have found that a geometric mean of 23 normal immune globulins was actually about 1:165,000. Accordingly, the RSV immune globulin produced from the selected plasma samples, based on the above findings, is expected to have a titer of about 1:600,000. Thus, the RSV immune globulin produced according to the method of this invention may have a titer of antibody to RSV of at least about 1:250,000 at a globulin concentration of about 5%, more preferably at least about 1:400,000, most preferably at least about 1:600,000. It should be understood that of the above limitations, the lowest limitation is considered critical to define the high titer anti-RSV immune globulin of the invention. Although an upper limitation, 1:1,000,000 is believed to be practicable, it is possible that higher titers could be obtained by further selection or by further concentrating the globulin.

The above-mentioned minimum antibody titers of the RSV immune globulin produced from selected plasma according to the method of the invention is based on a conventional concentration, i.e. 5%, solution of the high titer anti-RSV immune globulin. It is to be understood that it will be readily apparent to those skilled in the art to which this invention relates that, by concentrating the 5% solution, for example to a 10% or a 15% solution, the titers mentioned would be proportionately higher.

The method of screening the plasma, i.e., the ELISA method, is essentially as described by Engvall and Perlmann, *J. Immunol.*, 109, 129–135 (1972), Engvall et al, *Biochemica Et Biophysica Acta*, 251, 427–434 (1971), Engvall et al, *Immunochemistry*, 8, 871–874 (1971), which are all incorporated herein by reference. The assay is a simple method for the quantitative determination of antibodies. Microtiter plates coated with antigen are incubated with antiserum followed by an enzyme-labeled preparation of anti-globulin. The enzyme-labeled anti-globulin remaining in the wells after washing and quantitated by addition of a chromogenic substrate, provides a measure of the amount of specific antibodies in serum.

Plasma having a sufficiently high titer of antibody (an ELISA titer of at least about 1:110,000) is pooled and fractionated to obtain an immune globulin having a high titer of antibody to RSV. To this end one may employ any method for obtaining an intravenously injectable immune globulin from pooled plasma. For example, one may employ the Cohn fractionation method (referenced hereinbelow, which references are incorporated herein by reference thereto) an ammonium sulphate fractionation, polyethylene glycol precipitation or the like. The aforementioned immune globulin comprises IgG, usually at least 90% IgG monomer. The material generally also contains other globulins such as IgA, IgM, and the like.

These high titer plasmas are pooled and subjected to the Cohn fractionation method to produce Fraction II [Cohn et al, *J. Am. Chem. Soc.*, 68, 459 (1946) and Oncley, et al, *ibid.*, 71, 541 (1949)].

The so-obtained hyperimmune globulin may be rendered intravenously injectable by treatment according to the method of Tenold, "Intravenously Injectable Immune Serum Globulin", U.S. Pat. Nos. 4,396,608 and 4,489,073, or of Pappenhagen et al, "Pharmaceutical Compositions Comprising Intravenously Injectable Modified Serum Globulins, Its Production and Use", U.S. Pat. No. 3,903,262 (which are incorporated herein by reference) or any of the methods referred to in the above-identified U.S. patents. The method according to U.S. Pat. No. 3,903,262, broadly, involves modification of the immune globulin by reduction and alkylation to render it intravenously injectable. The method according to U.S. Pat. Nos. 4,396,608 and 4,499,073 involves adjusting the pH and ionic strength of a solution of the immune globulin to render it intravenously injectable.

The hyperimmune globulin preparation of this invention can also include maltose as a stabilizer in accordance with the teaching of U.S. Pat. No. 4,186,192. Accordingly, the instant preparation may contain about 1–20% of maltose on a weight to volume basis.

The hyperimmune products of the invention may be manufactured as pharmaceutical preparations, usually aqueous solutions of the hyperimmune globulin which may be used for prophylactic and therapeutic purposes. The products are sterilized by any suitable means, usually by sterile filtration through appropriate conventional media, in the manufacture of the pharmaceutical preparations.

The pharmaceutical preparation intended for therapeutic use should allow delivery of a therapeutic amount of hyperimmune globulin, i.e., that amount necessary for preventive or curative health measures in the treatment of infection by RSV.

The invention is demonstrated further by the following illustrative examples.

Assay Method

The ELISA method was essentially the same as that described by Engvall and Perlmann, *ibid.*, and used by Carlsson et al, *Inf. Imm.*, 6 (5) 703–708 (1972) for titration of anti-Salmonella immunoglobulins. The method has been previously adapted for microtiter plates [Voller et al, *Manual of Clinical Immunology*, 1976, 506–512], where visual endpoints can be determined with good sensitivity [Poxton, *J. Clin. Path.*, 32, 294–295 (1975), Voller et al, supra].

Round bottomed wells in polystyrene microtiter plates were sensitized by addition of 0.1 ml of the optimal dilution of RSV antigen in carbonate-bicarbonate buffer, pH 9.5, and incubated at 4° C. for approximately 18 hours. RSV antigen was obtained from MA Bioproducts (Walkersville, Md.), as crude, complement fixing antigen. Plates were washed once with phosphate buffered saline (PBS) containing 0.05% Tween 20 and 0.02% sodium azide (PBSTA). Five percent Bovine serum albumin (BSA), 0.1 ml was added to each well. The plates were further incubated 4–5 hours at room temperature, followed by one wash. The plates were shaken dry after the final wash. Dilutions of antisera were added to each well (0.1 ml) and incubated overnight at room temperature. Wells were washed three times as before and 0.1 ml of goat anti-human IgG conjugated to alkaline phosphatase (Miles Laboratories, Inc.) was added to each well and incubated 2 hours at room temperature. After again washing the wells, 0.1 ml of a 1.0% (w/v) solution of enzyme substrate, p-nitrophenyl phosphate, (Sigma Chemical Co.) in 10% diethanolamine buffer, pH 8.0, with 0.02% sodium azide and 1 mM Mg $Cl_2$ was added and incubated for 30 minutes, at room temperature. The reaction was stopped by the addition of 0.05 ml of 3N NaOH to each well. The absorbance was read at 405 nm with a Dynatech model 580 micro ELISA reader. The endpoint was taken to be the highest dilution with an absorbance $\geq 0.010$.

EXAMPLE 1

Plasma donations obtained from donors were screened for antibody to RSV by ELISA.

Plasma donations with an average RSV antibody titer of about 1:25,272 ("unselected") were pooled and fractionated according to the method of Pappenhagen et al, U.S. Pat. No. 3,903,262 to give an intravenously injectable "normal", immune globulin. The antibody titers of the "unselected" plasma pool and the "normal" immune globulin produced therefrom are set forth in Table 1.

Plasma donation samples with a geometric mean RSV antibody titer of about 1:106,738 were selected ("Selected Plasma Samples"). The geometric mean titer is set forth in Table 1 for comparison.

The fractionation method of Pappenhagen et al, U.S. Pat. No. 3,903,262 or that of Tenold, U.S. Pat. Nos. 4,396,608 and 4,499,073 may be used to produce the product according to the invention. Although the antibody titers of the RSV hyperimmune globulin produced by the method of Pappenhagen et al or by the method of Tenold are not available, it is expected that the antibody titers measured by ELISA will be substantially the same regardless of which method may be used. It is projected that the geometric mean titer of antibody to RSV should be about 1:533,690, that is about five times the titer of antibody to RSV in the "selected" plasma sample.

TABLE 1

| RSV Antibody Titers Determined by ELISA | |
|---|---|
| Test Sample Identification | ELISA Titer |
| Unselected Plasma Pool[a] | 1:25,272 |
| Normal Immune Globulin[b] | 1:165,534 |
| Selected Plasma Samples[c] | 1:106,738 |
| Hyperimmune Globulin[d] | 1:533,690 |

[a] = geometric mean of 24 unselected plasma pools.
[b] = geometric mean of 23 lots of immune globulin from unselected plasmas produced according to U.S. Pat. No. 3,903,262.
[c] = geometric mean of 39 selected plasma samples.
[d] = projected geometric mean of RSV hyperimmune globulin produced according to U.S. Pat. No. 3,903,262 or U.S. Pat. Nos. 4,396,608 and 4,499,073 from selected plasmas.

Given the above disclosure, it is thought that variations will occur to those skilled in the art. For example, by using anti-RSV monoclonal antibodies, it may be possible to produce such a high titer product. In the case of a very high titer immune globulin, it could be practical to administer the product intramuscularly. Therefore, it is intended that the above examples should be considered only illustrative and that the scope of the invention should be limited only by the following claims.

What is claimed is:

1. A method for raising serum antibody titers to respiratory syncytial virus in patients with or at risk of such infection by intravenously injecting a therapeutic amount of an intravenously injectable immune globulin having a titer of antibody to respiratory syncytial virus of at least about 1:250,000 at a globulin concentration of about 5% by weight, as determined by an enzyme-linked immunosorbent assay, which comprises the steps of:

(a) screening plasma from donors for a titer of antibody to respiratory syncytial virus of at least about 1:110,000, as determined by an enzyme-linked immunosorbent assay, (b) pooling the donor plasma selected according to step (a) above, (c) preparing an immune globulin from the plasma pooled according to step (b) above, and (d) rendering the immune globulin obtained according to step (c) above intravenously injectable.

2. A method according to claim 1 wherein, in step (c), the immune globulin is produced by the Cohn fractionation method.

3. A method according to claim 1 wherein, in step (d), the immune globulin is reduced and alkylated to render it intravenously injectable.

4. A method according to claim 1 wherein, in step (d), the immune globulin is provided in solution and the pH and ionic strength of the solution is adjusted so as to render it intravenously injectable.

5. An intravenously injectable immune globulin having a high titer of antibody to respiratory syncytial virus of at least about 1:250,000 at a globulin concentration of about 5% by weight, as determined by an enzyme-linked immunosorbent assay.

6. A pharmaceutical preparation comprising an amount of an intravenously injectable immune globulin according to claim 5 effective to treat infection by respiratory syncytial virus and a pharmaceutically acceptable carrier therefor.

7. A pharmaceutical preparation according to claim 8 further including maltose.

8. The globulin of claim 5 wherein the titer, at a globulin concentration of about 5% by weight in water, is in the range of about 1:250,000 to 1:1,000,000 as determined by an enzyme-linked immunosorbent assay.

* * * * *